United States Patent [19]

Schmidt

[11] Patent Number: 4,775,367
[45] Date of Patent: Oct. 4, 1988

[54] NEEDLE ASSEMBLY

[75] Inventor: Klaus J. Schmidt, Ahnatal, Fed. Rep. of Germany

[73] Assignee: B. Braun Melsungen AG, Melsungen, Fed. Rep. of Germany

[21] Appl. No.: 74,367

[22] Filed: Jul. 16, 1987

[30] Foreign Application Priority Data

Aug. 6, 1986 [DE]  Fed. Rep. of Germany ... 8621044[U]

[51] Int. Cl.⁴ ............................................. A61F 5/32
[52] U.S. Cl. ..................................... 604/192; 604/263
[58] Field of Search ............... 604/192, 187, 263, 199, 604/110, 111

[56] References Cited

U.S. PATENT DOCUMENTS

| | | | |
|---|---|---|---|
| 2,671,450 | 3/1954 | Dann | 604/192 |
| 2,847,996 | 8/1958 | Cohen et al. | 604/192 |
| 2,857,912 | 10/1958 | Feinstone et al. | 604/199 |
| 3,055,364 | 9/1962 | Myerson et al. | 604/192 |
| 3,272,322 | 9/1966 | Ogle . | |
| 3,865,236 | 2/1975 | Rycroft | 604/192 |
| 4,248,246 | 2/1981 | Ikeda | 604/263 |
| 4,253,463 | 3/1981 | Kim . | |
| 4,508,534 | 4/1985 | Garver, Sr. et al. | 604/111 |
| 4,610,667 | 9/1986 | Pedicano et al. | 604/192 |

*Primary Examiner*—John D. Yasko
*Attorney, Agent, or Firm*—Spensley Horn Jubas & Lubitz

[57] ABSTRACT

The needle assembly consists of a plastic cannula (11) with a hollow hub (12) at its dital end, a steel needle (16) adapted for insertion into the plastic cannula (11) and having a ground tip (17) and a needle head (15) adapted for being detachably coupled with the hollow hub (12), and of a tube-like protecting cap for the elongated parts. According to the inventon the protecting cap (22) has a closed, thick-walled bottom (23) into which the ground tip (17) of the steel needle (16) is clampingly pierceable, thus providing a reliable connection between these two parts. The steel needle (16) can be thrown into the commonly used waste containers without the protecting cap (22) falling off.

7 Claims, 1 Drawing Sheet

NEEDLE ASSEMBLY

BACKGROUND OF THE INVENTION

1. Field of the Invention

The invention refers to a needle assembly, consisting of a plastic cannula with a hollow hub at its distal end, a steel needle adapted for insertion into the plastic cannula and having a ground tip and a needle head adapted for being detachably coupled with the hollow hub, and a tube-like protecting cap for the elongated parts.

2. Description of the Related Art

In a needle assembly of this kind, the pointed steel-needle tip protruding beyond the blunt end of the plastic cannula effects the puncture of a blood vessel. After withdrawal of the steel needle, the plastic cannula serves as an in-dwelling cannula which remains in the blood vessel and has its hollow hub connected to a transfer device for infusion or transfusion of liquids. The free steel needle is disposed of. To prevent the medical staff and waste disposal personnel from being infected by punctures, e.g., with hepatitis or AIDS, it is necessary that the ground tip of the comparatively large-gauged steel needle be protected by attaching the protecting cap when thrown away. The precondition for such a protection, however, is a secure fastening of the protecting cap to the steel needle arrangement. This causes certain problems. When the needle assembly is ready for use, the open end of the protecting cap is clampingly plugged over an adapted extension of the hollow hub of the plastic cannula. The other end of the protecting cap, which can be open or closed by a bottom, extends for a length beyond the ground tip of the steel needle so that the steel needle is covered. If the open end of the protecting cap is clampingly plugged over the extension of the needle head, in a needle assembly having a short hollow hub of the plastic cannula, then the protecting cap will fit onto the withdrawn steel needle without being considerably elongated. However, the stability of this assembly depends on maintaining very narrow tolerances during production of the parts. Thus, even the basically simple protecting cap becomes an expensive special part. In needle assemblies in which the hollow hub of the plastic cannula is provided with fixing plates for attachment on the skin of the patient, there is the disadvantage that the protecting cap is considerably shorter than the steel needle. Thus, after being withdrawn from the plastic cannula, the steel needle cannot be assembled with the extension of the needle head forming a connection with the protecting cap. To allow plugging of the protecting cap onto the steel needle after puncture so that the needle can be disposed of, the protecting cap must have an additional length in the range of the longitudinal extension of the fixing plates. This, however, increases the packing and transport volume of such needle assemblies by about 20 percent (20%), thus raising the costs.

SUMMARY OF THE INVENTION

It is an object of the invention to improve a needle assembly of the initially mentioned type in such a manner that, for disposal of the steel needle, the protecting cap, being adapted to the length of the telescoping assembly of plastic cannula and steel needle, can be firmly connected with the steel needle independently of the length of the withdrawn steel needle itself.

According to the preferred embodiment of the invention, the protecting cap has a closed thick-walled bottom into which the ground tip of the steel needle is clampingly pierceable. The ground tip of the steel needle is used for connecting the steel needle withdrawn from the plastic cannula to the protecting cap. The fact that the length of the plastic cap, being adapted to the length of the plastic cannula, is too short for the withdrawn steel needle, is unsubstantial for the connection of both parts.

In accordance with the preferred embodiment of the invention, the end of the protecting cap at the side of the ground tip is formed in such a manner that the ground bevel of the steel needle can be firmly inserted into the thick-walled bottom after use, thus providing a reliable connection between these two parts. Thereafter, the steel needle can be thrown into the commonly used waste containers without the protecting cap falling off. In this manner, the increasing demand for security for avoiding infections such as AIDS is completely met. The effect of the improvement according to the invention is particularly advantageous in needle assemblies with fixing plates, as the packing and transport volume of the needle assembly is not increased by extremely long protecting caps, thereby avoiding an increase in costs.

In one embodiment of the invention, the depth of the thick bottom corresponds, at least, to the single length of the ground level of the needle tip, and at the most, to the triple length thereof. The ground tips of the steel needles are very sharp and can be easily pressed into the plastic material of the protecting cap, whereby the indicated dimensions of the thickness of the bottom ensures that the tip does not penetrate the bottom.

The inner surface of the bottom can be nonprofilated and smooth. For preventing the ground bevel of the steel needle from emerging out of the thin jacket of the protecting cap, a centering of the ground tip upon insertion is recommended. To this effect, the inner surface of the bottom can be formed as a conical, pointed recess. The tip of the bottom recess, situated on the central axis of the protecting cap or offset to the side of the central axis, necessarily causes a substantially central insertion of the steel-needle tip into the thickened bottom of the protecting cap.

Preferably, the pointed recess has its walls provided with axial clamping ribs symmetrically narrowing the free cross-section of the recess. The clamping ribs can consist of solid arms being convexly curved against the central axis of the protecting cap and forming between them a narrow channel for clampingly receiving and holding the ground tip of the steel needle. Three clamping ribs, equidistantly distributed over the circumference of the pointed recess, serve for sufficiently guiding and holding the tip of the steel needle.

In another embodiment of the invention, the inner surface of the bottom can be provided as an eccentrically wedge-shaped recess for causing engagement between the needle tip and the protecting cap. In this case, the steel needle slides along the inner wall of the protecting cap into the eccentrically wedge-shaped recess, and its sharp tip penetrates eccentrically into the substance of the thick bottom of the protecting cap. In all these cases, a secure holding engagement between protecting cap and puncture needle is obtained without the open end of the protecting cap being coupled with an extension of the needle head.

By means of injection molding, the protecting cap is produced in one piece as a tubular body with outer axial stiffening ribs. Between the stiffening ribs, gas inlet openings are arranged in the wall of the protecting cap. Through these openings, the steel needle to be disposed of can be sterilized by ethylenoxid gas with the protecting cap mounted. This procedure, too, contributes to the safety when disposing of the steel needles.

BRIEF DESCRIPTION OF THE DRAWINGS

Embodiments of the invention are systematically shown in the drawings, in which.

DESCRIPTION OF THE PREFERRED EMBODIMENT

Figure 1:
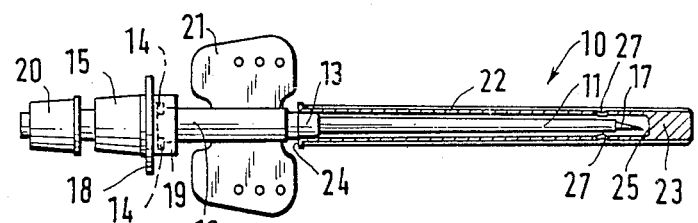
FIG. 1 is a plan view of an embodiment of a complete needle assembly.

The needle assembly 10 generally consists of a flexible plastic cannula 11 being fastened with one end to a hollow hub 12 which has, at its end adjacent the cannula, an extension 13 and, at the edge of the opposite end, two radial projections 14 being circumferentially wedge-shaped. The cavity of hub 12 is formed as an innercone for receiving connecting members. Such a connecting member is provided at a needle head 15, which holds a coaxial steel needle 16, the pointed sharp tip 17 of which in FIG. 1 protrudes beyond the truncated end of the plastic cannula 11. A grip plate 18 normally projects from the needle head 15, and has, at one side, a jacket member 19 joined thereto. When the hub 12 and the needle head 15 are assembled, the jacket member 19 surrounds the end of hub 12, with the radial projections 14 which are received in corresponding longitudinal recesses of jacket member 19. A closing cap, particularly a blood-indicating plug 20, is mounted on the distal end of needle head 15. Two fixing plates 21 extend from hub 12 traversely to its longitudinal axis and serve for fastening the assembly on the skin of the patient by adhesive tapes. If needed, these fixing plates 21 can be foldable.

The needle assembly 10, being arranged in a sterile packing and being ready for use, further comprises a protecting cap 22. This protecting cap 22 is integrally molded in one piece by puncturable, yielding plastic material and has its one end closed by a thick-walled bottom 23, whereas its other end is provided with an opening 24 for being clampingly plugged onto the extension 13 of the hollow hub 12. The length of the cylindrical cavity 34 of protecting cap 22, between the inner surface 25 of the bottom 23 and opening 24, is such that in the shown assembled condition of protecting cap 22, the tip of the steel needle 16 does not touch the inner surface 25 of the bottom 23. The bottom 23 is thick and adapted to be pierced. Its minimal depth corresponds generally to the single length of the bevelled portion 17a of the eccentric tip 17 of the steel needle 16, and its maximal depth corresponds to the triple length thereof. On the outer circumference of protecting cap 22, longitudinal stiffening ribs 26 are arranged at an equal distance. Between these ribs, there are arranged at least two diametrically opposed gas inlet openings 27 which, in the shown example, are formed as longitudinal slots. In altered embodiments, the gas inlet openings can be bores with arbitrary contours.

After drawing off protecting cap 22 from extension 13, a blood vessel, into which plastic cannula 11 is to be inserted as an in-dwelling vein catheter, is punctured by means of tip 17 of steel needle 16 protruding beyond plastic cannula 11. After successful puncture, which can be checked by the blood-indicating plug 20, the steel needle 16 is axially withdrawn from hub 12, by separating needle head 15 from hub 12, and the plastic cannula 11 is advanced into the blood vessel as far as required. Then, the unit, consisting of plastic cannula 11 and hub 12, is fastened on the skin of a patient by fixing plates 21.

Figure 2:
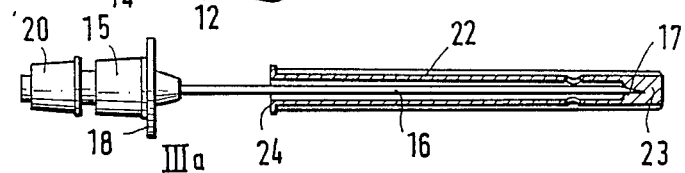
FIG. 2 is a plan view of an embodiment of a steel needle with protecting cap when withdrawn from the plastic cannula.

To prevent the free steel needle from puncturing and, thus, infecting the medical staff and the waste disposal personnel, the steel needle must be tightly connected to a cover. When the assembly is to be disposed of, protecting cap 22 is used as a cover. As FIG. 2 shows, protecting cap 22 is, by the length of hub 12, shorter than steel needle 16. As a result, it is impossible to assemble opening 24 of the protecting cap 22 with the connecting member of needle head 15 so as to connect both parts. Therefore, according to the preferred embodiment of the invention, the connection is effected at the patient-side end of the assembly. To this purpose, the sharp ground tip 17 of the steel needle 16 is pierced into the thick bottom 23 of protecting cap 22 so that a tight fit is obtained. During this procedure, the thickness of bottom 23 prevents that, while tip 17 penetrates bottom 23 and indeed effects a firm connection between steel needle 16 and protecting cap 22. The tip 17, however, is not rendered harmless. As shown in FIGS. 1 and 2, the inner surface 25 of bottom 23 of protecting cap 22 generally extends perpendicularly to the longitudinal axis of protecting cap 22 and is flat. Thus, there is no guidance for the tip 17 when it is pierced into the bottom 23 and the tip 17 penetrates the bottom 23 at any random point. This arrangement constitutes the simplest embodiment of the invention which can be improved by different modes of centering tip 17 upon insertion.

Figure 3:
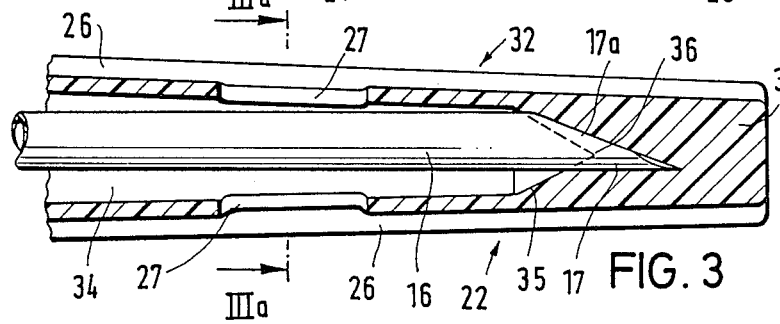
FIGS. 3 and 3a are a longitudinal section and a cross section, respectively, of a further embodiment of the bottom of the protecting cap.
Figure 3A:
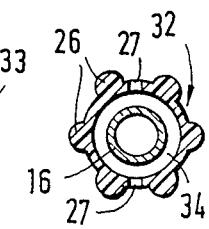

Such modes of centering, for facilitating insertion of tip 17, are realized by the embodiments of the invention as shown in FIGS. 2 to 5. According to FIGS. 3 and 3a, the inner surface 35 of the thick bottom 33 of the protecting cap 32 is provided with a pointed tapered recess that has its tip 36 slightly offset with regard to the central axis of protecting cap 32, thus, facilitating guidance of the eccentric tip 17 of the steel needle 16 upon insertion into bottom 33. In the assembled condition of steel needle 16 and protecting cap 32, the steel needle 16 extends obliquely within the cavity 34, tapering towards bottom 33 and having a circular cross section. This, however, is of no importance for the firm connection of the parts to be disposed of.

Figure 4:
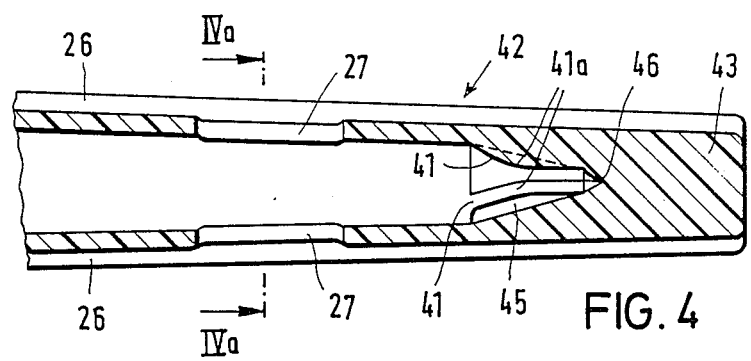
FIGS. 4 and 4a are a longitudinal section and a cross section, respectively, of a third embodiment of the bottom of the protecting cap.
Figure 4A:
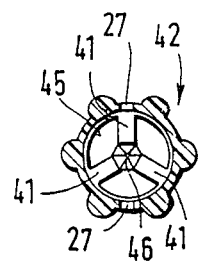

In the example according to FIGS. 4 and 4a, a protecting cap 42 comprises an altered bottom 43. This bottom 43 is thick-walled, but, for facilitating insertion of tip 17 of steel needle 16 and effecting a sufficiently firm connection between protecting cap 42 and steel needle 16, is provided with a modified inner surface shape 45. The inner surface 45 extends longitudinally and is formed as a pointed cone. The prism-shaped tip 46 of the cone is positioned on the central axis of protecting cap 42. On the inner surface 45 of bottom 43, which tapers to a point in length wise direction, three clamping ribs 41 are formed at equal distances to each other. These clamping ribs extend axially form tip 46, and have convex backs which are radially directed towards the central axis of protecting cap 42. Each clamping rib 41 forms a radial projection 41a. The three clamping ribs 41 symmetrically narrow the free cross section of the recess defined by inner surface 45 in such a manner that the inner surface 45 forms a channel. This channel serves both for guiding tip 17 of steel needle 16 to be inserted and for clampingly holding tip 17. By being further pushed forward, tip 17 of steel needle 16 is pierced into the thick bottom 43 for optimum consistency of the parts. As shown in FIG. 4a, tip 46 has a prism-shaped profile.

Figure 5:
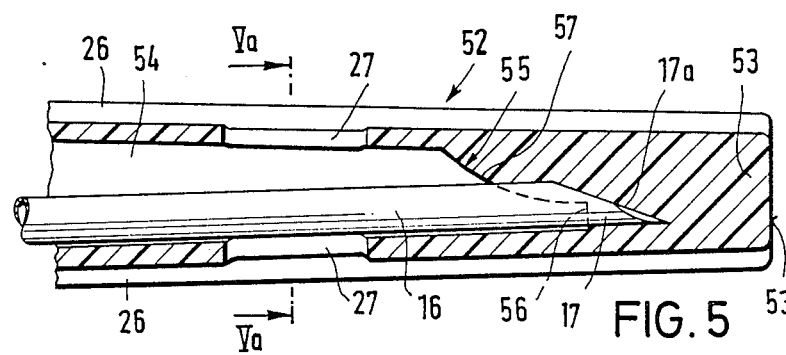
FIGS. 5 and 5a are a longitudinal section and a cross section, respectively, of a fourth embodiment of the bottom of the protecting cap.
Figure 5A:
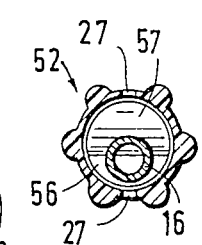

In the embodiment according to FIGS. 5 and 5a, bottom 53 of a protecting cap 52 is thickened, and its inner surface 55 has its profile eccentrically recess in a wedge-shape. The profile of inner surface 55 is generally obtained by a convex, inwardly directed projection 57. The projection 57 extends from the inner wall of a transverse half of protecting cap 52, beyond the central axis of protecting cap 52, towards the end wall 53A of bottom 53, and, at its end, changes into a short transverse surface 56, which is generally perpendicular to the central axis and which joins the inner wall of the other transverse half of protecting cap 52. A steel needle 16, pushed into protecting cap 52, slides along the inner wall of cavity 54 of protecting cap 52 and, with the bevelled portion of its ground tip 17, hits the inwardly directed projection 57 of inner surface 55. The needle is, thereby, immediately directed against the transverse surface 56, which is punctured by tip 17. Bottom 53 is pierced by steel needle 16 until a section of the cylindrical part of the steel needle sticks in bottom 53. Also this connection between steel needle 16 and protecting cap 52 is durable and firm, thus, the used steel needle can be disposed of without any danger for the medical staff or the waste disposal personnel.

I claim:

1. A needle assembly, comprising:
   a cannula having a hollow hub at its distal end;
   a needle, adapted for inserting into said cannula, said needle having a ground tip and a needle head adapted for detachably coupling with said hollow hub; and
   a tubular protecting cap having a closed, thick-walled bottom into which said ground tip of said needle is clampingly pierceable,
   said protecting cap having an opening therein and defining a cavity between said thick-walled bottom and said opening, said cavity defined by said protecting cap being configured such that said ground tip of said needle does not touch said thick-walled bottom when said hollow hub is coupled with said needle head,
   said protecting cap being shorter than said needle by the length of said hollow hub,
   whereby said ground tip is permitted to be imbedded in said thick-walled bottom when said hollow hub is not coupled with said needle head.

2. A needle assembly according to claim 1, wherein said thick-walled bottom of said protecting cap has a minimal depth corresponding to the single length of said ground tip of said steel needle and a maximal depth corresponding to the triple length thereof.

3. A needle assembly according to claim 1, wherein said thick-walled bottom has an inner surface formed as a conical, pointed recess.

4. A needle assembly according to claim 3, wherein said pointed recess has a wall provided with axial clamping ribs, narrowing the cross section of the recess.

5. A needle assembly according to claim 1, wherein said thick-walled bottom has an inner surface being eccentrically recessed in a wedge shape.

6. A needle assembly according to claim 1, wherein said protecting cap is formed in one piece, as a tubular body having external axial stiffening ribs, by injection molding.

7. A needle assembly according to claim 6, further comprising:
   gas inlet openings arranged in the wall of the protecting cap, between said stiffening ribs.

* * * * *